(12) United States Patent
Borneman et al.

(10) Patent No.: US 6,248,307 B1
(45) Date of Patent: Jun. 19, 2001

(54) COMPOSITIONS AND TREATMENT FOR ALLEVIATION OF SYMPTOMS ASSOCIATED WITH MENOPAUSE

(75) Inventors: John P. Borneman, Bryn Mawr, PA (US); Mark S. Phillips, Huntington Beach, CA (US)

(73) Assignee: Standard Homeopathic Company, Los Angeles, CA (US)

( * ) Notice: Subject to any disclaimer, the term of this patent is extended or adjusted under 35 U.S.C. 154(b) by 0 days.

(21) Appl. No.: 09/519,692

(22) Filed: Mar. 7, 2000

Related U.S. Application Data

(60) Provisional application No. 60/129,180, filed on Apr. 14, 1999.

(51) Int. Cl.[7] ............................. A61K 35/78; A61K 9/48; A61K 9/20; A61K 9/28; A61K 9/14
(52) U.S. Cl. .................. 424/45 L; 424/464; 424/474; 424/489; 424/195.1
(58) Field of Search .................... 424/451, 464, 424/474, 489, 195.1, 400

(56) References Cited

U.S. PATENT DOCUMENTS

| | | |
|---|---|---|
| 5,565,199 | 10/1996 | Page et al. . |
| 5,569,459 | 10/1996 | Shlyankevich . |
| 5,654,011 * | 8/1997 | Jackson et al. . |
| 5,707,630 | 1/1998 | Morrow . |

OTHER PUBLICATIONS

Hyland's Menopause oif Hyland's Homeopathic Remedies see webpage "http://www.getset.com/uptown/hyremedy.html".*

"Le Science et L'Art de Guerir" C.M. Boger see webpage "http://www.homeoint.org/books.bogsci/default.htm".*

Black Cohosh, A Woman's Herb Comes of Age, Hobbs, Herbs for Health, Mar/Apr. 1998, pp. 38–41.

"Was Lydia E. Pinkham's Vegetable Compound an Effective Remedy", Tyler, Pharmacy in History, vol. 37 (1995), pp. 24–28.

* cited by examiner

*Primary Examiner*—Thurman K. Page
*Assistant Examiner*—Amy E Pulliam
(74) *Attorney, Agent, or Firm*—Fulbright & Jaworski, LLP

(57) ABSTRACT

A composition having at least one herbal compound and at least one homeopathic drug is useful for treating symptoms associated with menopause. Methods of preparing the composition and methods of treating, alleviating or otherwise mitigating the menopausal symptoms are also described.

9 Claims, No Drawings

COMPOSITIONS AND TREATMENT FOR ALLEVIATION OF SYMPTOMS ASSOCIATED WITH MENOPAUSE

This application claim benefit to provisional application No. 60/129,180 Apr. 14, 1999.

TECHNICAL FIELD

The present invention relates to a composition having at least one herbal compound and at least one homeopathic drug that is useful for treating symptoms associated with menopause. Methods of preparing the composition and methods of treating, alleviating or otherwise mitigating the menopausal symptoms are the subject of the present invention.

BACKGROUND AND SUMMARY OF THE INVENTION

Menopause is the termination of the menstrual cycle in woman, and is caused by the changes in hormone levels that occur naturally over time. Estrogen and progesterone are the key hormones involved in these changes, but other factors may be involved as well.

The onset of menopause is associated with many symptoms will vary between women, but will generally include one or more of the following symptoms: hot flashes, numbness, tingling, insomnia, nervousness, depression, vertigo, fatigue, arthralgia, myalgia, headaches, palpitations, and formication. Osteoporosis is another condition associated with the onset of menopause, and leads to decreased bone density and an increase in fractures and breaks.

Menopausal symptoms are related primarily to the change in estrogen levels, and estrogen replacement therapy, either with or without progesterone, is a common method of providing some relief from menopausal symptoms. However, hormone replacement therapy is associated with many adverse effects, potentially leading to problems are potentially more troublesome than the menopausal symptoms themselves. Calcium may be added to the regimen to combat or prevent the effects of osteoporosis.

Other, methods for treating the symptoms associated with menopause are known. For instance, there are several herbal remedies that are used to alleviate menopausal symptoms; homeopathic remedies are known as well. Presently available formulations consist of either herbs or homeopathics; combination formulations of herbal and homeopathics are not presently believed to be available. One example of a commercially available homeopathic remedy for treatment of menopausal symptoms is Hyland's Menopause Tablets, which contains a specific combination of Amyl Nitrosum, *Sanguinaria Canadensis* and *Lachesis Mutus* in a lactose base. Other known homeopathic products useful in treating various conditions are described in the Homeopathic Pharmacopeia of the United States(HPUS).

Despite the advances in the art, there is a need for improved therapies for treating menopausal symptoms. Thus, it is an object of the present invention to provide improved formulations for the treatment and prevention of menopausal symptoms.

It is also an object of the present invention to provide improved methods for preparing formulations, particularly oral solid dosage forms, useful in treating menopausal symptoms.

It is also an object of the present invention to provide improved methods of treating, preventing or otherwise mitigating the symptoms associated with menopause.

These objects and others are achieved by the present invention, which related in part to an oral solid dosage form that includes from about 1 to about 99 wt. % of a therapeutically effective amount of at least one herb that renders a therapeutic effect on menopausal symptoms, and from 1 to about 99 wt. % of at least one homoeopathic component that renders a therapeutic effect on menopausal symptoms, wherein the weight percent is based on the total amount of the homeopathic and herbal components. For purposes of this invention, rendering a therapeutic effect on menopausal symptoms is defined as reducing the severity or incidence, preventing, or otherwise alleviating at least one symptom associated with menopause. In preferred embodiments, the herbal component will include *Cimicifuga Racemosa*, and the homeopathic component will include Amyl Nitrate. In other preferred embodiments, the oral solid dosage form provides a sustained release of one or more active components in vivo for a time period of from 6 to about 24 hours.

In a preferred embodiment, the oral solid dosage form also contains a calcium salt, e.g. calcium citrate. When calcium is present, it is preferred that at least 200 mg calcium ion be provided by the dosage form. Preferred dosage forms include tablets and capsules.

The present invention also relates to a method of preparing an oral dosage form for the treatment of menopausal symptoms. The dosage forms may be prepared by admixing the requisite amounts of homeopathic drug and herbal components, together with the calcium salt any pharmaceutical excipients, and dividing the mixture into unit doses containing an appropriate amount of the admixture to treat menopausal symptoms when administered to a patient in need of such treatment.

The present invention also relates to a method of treating menopausal symptoms by administering a unit dose of the combination of the present invention to a patient in need of treatment for menopausal symptoms.

The invention is described in more detail in the description that follows.

DETAILED DESCRIPTION OF THE PREFERRED EMBODIMENTS

The oral solid dosage forms of the present invention are a therapeutically active blend of herbs and homeopathic drugs that provide relief for patients suffering from menopausal symptoms. The herbal component preferably comprises from about 1 to about 99% by weight of the combined weight of the herbal and homeopathic components form, and preferably between about 25 to 75% by weight.

Any herb that is capable of providing relief from menopausal symptoms may be included in the dosage form, provided it is not incompatible with the other ingredients. A non-limiting list of suitable herbs that may be used in accordance with the present invention include wild yams, black cohosh, and the like. The herb will be present in an amount ranging from 1 to about 99 wt % of the combined weight of the herb(s) and homeopathics, preferably between about 25 and 75% by weight.

It is preferred that black cohosh is included as one of the herbal components. Also known as black snakeroot and actaeae racemosae radix, black cohosh consists of the dried roots and rhizomes of *Cimicifuga racemosa*. Pharmacologic studies have shown that black cohosh contains several compounds which may contribute to its activity, including triteipene glycosides, aglycones, isofalvones, and aromatic acids. It has been demonstrated that black cohosh may exert its effect on menopausal woman by reducing the serum concentration of the pituitary hormone luteinizing hormone (LH) (Duker, E. M. et al., Effects of extract from *Cimicifuga racemosa* on gonadotropin release in menopausal women and ovariectomized rats. *Planta Medica,* 57:420–424.) It is preferred that from about 40 to about 3000 mg of the dried root and rhizome be provided, daily, preferably from 100 to 400 mg. Alternatively, a sufficient amount of black cohosh is provided to deliver between 2 and 10 milligrams of triterpene glycosides and preferably from about 3 to about 5 mg daily. Thus, an equivalent amount of black cohosh extract may be included. Most preferably, a sufficient amount of black cohosh or equivalent is provided to provide 4 mg tritrerpene glycosides per day. The dosage form preferably contains 2 mg triterpene glycoside, and two dosage forms will be administered per day. In another preferred embodiment, the dosage form provides 1 mg triterpene glycosides and four dosage forms are administered daily.

The homeopathic drug included in the dosage form will comprise from about 1 to about 99% by total weight of the herbal component and the homeopathic component. Suitable homeopathics that may be included in the oral solid dosage form of the present invention include Amyl Nitrate, *Sanguinaria Canadensis, Lachesis Muta,* and the like. Amyl nitrate (amyl nitrosum) is a mixture of the nitrite esters of 3-methyl-1-butanol and 2-methyl- 1-butanol which has been reported to provide relief from certain menopausal symptoms, including hot flashes. It contains not less than 85% and not more than 103% $C_5H_{11}NO_2$. The dosage form will typically include from about 2× ($10^{-2}$M) to 10× ($10^{-10}$M) to about 150 mg amyl nitrate, preferably from about 5× to about 10×.

*Sanguinaria Canadensis,* also known as bloodroot, is a perennial plant that derives its name from the red, cylindrical rhizome. It thrives in the open woods and along shaded streams in the United States and Canada. Sanguinaria has been reported to provide relief from hot flashes due to menopause. The dosage form will contain from about 10 to about 50 mg of sanguinaria, preferably from about 15 to about 20 mg calculated as the root and rhizome, or the therapeutically effective amount of sanguinaria extract or other preparation.

*Lachesis muta* is also preferably included in the dosage form. *Lachesis mutus* is a tropical South American venomous snake commonly known as the Bushmaster. The venom of this snake has been reported to reduce palpitations, the incidence or severity of hot flashes, and headache associated with menopause.

Preferred dosage form also contain a source of calcium ions. Calcium, when taken in appropriate quantities through diet and/or supplement, has been shown effective to reduce effects of osteoporosis, a condition often associated with menopause. Preferably, between 200 mg and 1000 mg of elemental calcium is provided in the dosage form, preferably 400 to 800 mg elemental calcium as a calcium salt, complex, or other calcium source. Preferably, the dosage form provides from about 250 to about 500 mg calcium. Preferred calcium sources included calcium salts such as calcium citrate, calcium carbonate, calcium lactate, and the like. Calcium citrate is a preferred calcium salt for inclusion in the dosage form of the present invention because of its excellent absorption qualities. Calcium citrate contains 21% elemental calcium.

Suitable amounts of pharmaceutical adjuvants, e.g. binders, colorants, processing aids, compression aids, fillers will be included as necessary in appropriate amounts.

The final oral dosage form may be a powder, dragee, capsule, tablet or powder for suspension. A preferred dosage form is a tablet.

When the dosage form is a tablet, the tablets are preferably coated to enhance the quality of the final product. The coating may also be a sustained release coating to sustain the release of one or more of the active components of the tablet. The coating may also be an enteric coating, so that the active components are released in the intestine rather than in the acidic environment of the stomach.

A preferred oral solid dosage form according to the present invention is a tablet containing 40 mg of CimiPure® commercially available from Madis Botanicals which is standardized to provide 1 mg triterpene/40 mg extract. CimiPure® is a preferred source of black cohosh extract, but others may be used as well. A preferred final dosage form contains 4 mg of black cohosh triterpene glycosides, 130 mg of homeopathics, and 953 mg of calcium citrate, along with processing aids and coatings such that the tablet weighs 1300 mg. This dosage form will preferably be administered on a two-tablet, twice daily basis (for a total of four tablets daily) to a person in need of relief from menopausal symptoms, particularly hot flashes. A most preferred embodiment provides Amyl Nitrosum 6× ($10^{-6}$M) HPUS; *Sanguinaria Canadensis* 12× ($10^{-12}$M) HPUS; *Lachesis Muta* 12× ($10^{-12}$M) HPUS; *Cimicifuga Racemosa* 10 mg rhizome standardized to provide 4 mg triteipene glycosides; and at least 200 mg calcium provided as calcium citrate. It should be understood that any of the ingredients may be provided in a suitable form, e.g. an extract, powder, whole herb, etc., provided the final product contains the requisite effective amount of ingredients.

Incidentally, to convert the homeopathic units, e.g., 6× to milligrams, simply divide the weight of the tablet in milligrams by $10^X$. For example, a 1300 mg tablet containing 3×Sanguinaria=1.3 mg Sanguinaria per tablet.

It is preferred that the dosage form retain the original HPUS strength of dilution.

The dosage forms of the invention may also contain pharmaceutical excipients such as fillers, colorants, flavorants, lubricants, and the like. Typically, the dosage form will comprise from about 1 to about 15% by weight pharmaceutical excipients, and preferably less than 15%. The dosage forms of the present invention are prepared by admixing the herbal component together with the homeopathic component, and dividing the mixture into unit doses of desired strength, preferably such that each unit does provides an effective amount of herbal and homeopathic components to provide relief from menopausal symptoms when administered to a patient in need of such relief. It is contemplated that, due to physical limitations, a unit does may be subtherapeutic but can be formulated to provide an effective does when administered in multiple, i.e. two or more, unit doses or dosage forms at a time. The unit dose is preferably then encapsulated or tableted according to conventional techniques. To prepare the finished dosage form, the herbal and homeopathic components may be admixed with pharmaceutical adjuvants and encapsulated or tableted or otherwise prepared as known in the art.

The oral solid dosage form may then be coated, which is particularly desirable if the dosage form is a tablet. Coating may be accomplished using known equipment and techniques.

Treatment of menopausal symptoms is accomplished by orally administering the dosage forms of the present invention to a patient in need thereof. The term treatment is used in its broadest sense and, as used herein, means lessening the severity, preventing, or otherwise alleviating menopausal symptoms, including prophylaxis.

Administration may be as a single dose, or on a multiple dosing schedule, e.g. twice or three times daily.

The following examples are illustrative of preferred embodiments of the invention.

DETAILED DESCRIPTION OF PREFERRED EMBODIMENTS

EXAMPLE 1

Tablets according to the present invention are prepared as follows:

An 87% ethyl alcohol solution in distilled water is prepared by adding an appropriate volume of the alcohol (USP) to distilled water (NF). Amyl Nitrosum (5× HPUS Dilution) and *Lachesis Muta* (9× HPUS Dilution) are added to the 87% ethyl alcohol solution and mixed to completion. This mixture is added to a sufficient quantity of Lactose N.F. in a mixer, along with a sufficient quantity of *Sanguinaria Canadensis* Mother Tincture, and mixed to completion. This mixture is then dried and removed to a Sherman triturator and triturated to completion to form the premix.

An appropriate amount of the premix is combined with microcrystalline cellulose, croscarmellose sodium, vegetable stearate, acid, and silicon dioxide, mixed, and oscillated through a 20 mesh screen. Calcium citrate is combined with this screened mix and mixed.

*Cimicifuga Racemosa* Standardized Powder Extract (CimiPure®) is oscillated through a 50 mesh screen. This is combined with the homeopathic/calcium mix and mixed to completion. This mix is combined with vegetable magnesium stearate, mixed to completion, and tableted to form 1300 mg oral tablets. The tablets are coated with an aqueous ethylcellulose dispersion in a coating pan, and dried. The resultant tablets contain 200 mg elemental calcium, Amyl Nitrosum 6× ($10^{-6}$M) HPUS, *Sanguinaria Canadensis* 3× ($10^{-3}$M) HPUS, *Lachesis muta*($10^{-12}$M) 12× HPUS, *Cimicifuga Racemosa* (standardized to provide 1 mg triterpenes), and 14% excipients.

EXAMPLE 2

A study was conducted on a group of six women ages 35–70 with a history of hot flashes for at least one month and with an average of at least three hot flashes per day in the week prior to beginning the study. These were selected from a pool of applicants based on the following criteria: Patients who were currently pregnant or breast feeding, who had active influenza infection, or who were taking any medications for the treatment of hot flashes, including estrogens, androgens, progestational agents, corticosteroids, DHEA, yam extracts, herbs, or chemotherapy were excluded. Also excluded were patients who were taking vasodilators or other cardiac medications. Patients with a past history of any of these agents must have discontinued them for at least one month prior to entry into the study.

Patients enrolled into the study were evaluated to assess their Kupperman index to determine the severity of menopausal symptoms at entry into the study (Kupperman, 1953, see below). Two additional symptoms were added to the Kupperman index-vaginal dryness and painful intercourse. Subjects were also given a self-administered daily diary questionnaire to record the frequency and severity of hot flashes over the next four weeks. For the first week, they were instructed not to take any medication, but to simply record the information about hot flashes on the questionnaire. At the end of the baseline week, they were instructed to continue the diaries, but also to begin taking two tablets according to Example 1 twice daily for the following three weeks. They were also asked to note any possible side effects of the medication.

At the end of two weeks, a study nurse called the patients to monitor progress and address any patient concerns. At the end of four weeks, the patients returned to the clinic, the diaries were collected, and the Kupperman index was administered again to evaluate changes in severity of global menopausal symptoms. Patients were also instructed to return their vials of remaining medication, and the number of pills will be counted to evaluate compliance.

Statistical analysis was done using the Epi-info statistical program. Three variables were used to assess the efficacy of treatment before and after taking the tablets of Example 1. The average number of hot flashes per day, the average daily hot-flash score, and the Kupperman index. The average daily hot-flash score for each patient was calculated by adding the total number of mild hot flashes plus twice the number of moderate hot flashes plus three times the number of severe hot flashes recorded in a given week and then dividing the sum by the number of days on which values were recorded.

Six women were evaluated in this preliminary analysis. All were white Caucasian, non-smoking, and had some college education. Their average age was 51.4 years (range 50.1–55.9). The average Kupperman index was 23.67 (SD 11.29) at entry into the study, with an average frequency of hot flashes of 5.16/day (SD 2.05) and a mean hot-flash score of 8.14 (SD 2.24).

After three weeks of treatment, the average Kupperman index was 13.83 (SD 9.93), which represented a 41.6% decrease in symptoms (p=0.13). (Table 1) The average number of hot flashes at the end of three weeks had decreased by 54.7% to 2.34 (SD 1.79) (p=0.04) and the hot-flash score had been reduced by 53.3% to 3.80 (SD 3.21) (p=0.03). Two women reported mild gastrointestinal symptoms that resolved after the first week of the medication. One woman noticed an increase in the duration of her menstrual period, while another mentioned that the spotting between menses that she had for the previous five months was resolved. All of the women returned empty bottles of study medication.

The results, summarized in Table 1 below, showed a decrease in hot flashes and other menopausal symptoms with a high compliance rate and a low rate of side effects.

TABLE 1

Comparison of mean symptom scores (with standard deviation) before and after three weeks treatment with Tablets of Example 1.

| | Baseline | After 3 weeks | p-value* |
|---|---|---|---|
| Kupperman index | 23.67 (11.29) | 13.83 (9.93) | 0.13 |
| Hot flash frequency/day | 5.16 (2.05) | 2.34 (1.79) | 0.04 |
| Hot flash score/day | 8.14 (3.42) | 3.80 (3.21) | 0.03 |

*Paired t-test used

To aid with the understanding of the methodology used in this test, a Kupperman Menopausal Index Score Example case is provided below:

| Kupperman Menopausal Index Score- Example case | | | |
|---|---|---|---|
| Symptoms | Factor | Severity | Numerical Conversion |
| Hot Flashes | 4 | 3 | 12 |
| Numbness/tingling | 2 | 2 | 4 |
| Insomnia | 2 | 2 | 4 |
| Nervousness | 2 | 1 | 2 |
| Depression | 1 | 0 | 0 |
| Vertigo | 1 | 0 | 0 |
| Fatigue | 1 | 2 | 2 |
| Arthralgia/myalgia | 1 | 1 | 1 |
| Headaches | 1 | 3 | 3 |
| Palpitation | 1 | 2 | 2 |
| Formication | 1 | 1 | 1 |
| Vaginal dryness | 2 | 1 | 2 |
| Low sex drive | 2 | 2 | 4 |
| Menopausal Index (SUM) | | | 37 |

Factor: Weighted score for the prevalence and importance of that symptom in menopause.

Remains the same for all patients. Italicized factors added to original Kupperman index.

Severity: None=0, Slight=1, Moderate=2, Marked=3. Varies from patient to patient.

Numerical Conversion: Value of Factor X Severity

Menopausal Index: Sum of numerical conversions for all symptoms.

It is claimed:

1. An oral dosage form comprising:
    at least one homeopathic drug selected from the group consisting of Amyl Nitrosum, *Lachesis Muta* and *Sanguinaria Canadensis;*
    an herbal component comprising *Cimicifuga Racemosa*; and
    a calcium salt.

2. The oral dosage form of claim 1, in a form selected from the group consisting of a capsule, dragee, powder for reconstitution, and tablet.

3. The oral dosage form of claim 2, in the form of a tablet.

4. The oral dosage form of claim 3, further comprising a cellulose tablet coating.

5. The oral dosage form of claim 4, further comprising from 5 to 15% by weight pharmaceutical excipients.

6. A method of preparing an oral solid dosage form comprising admixing sufficient amount of Amy Nitrosum, *Lachesis Muta, Sanguinaria Canadensis, Cimicifuga Racemosa* and calcium citrate to form a mixture, and dividing the mixture forming oral solid dosage forms.

7. A method of treating menopausal symptoms comprising administering the oral solid dosage form of claim 1 to a patient in need thereof.

8. A tablet for treatment of menopausal symptoms comprising: 1 mg of black cohosh triterpene glycosides, Amyl Nitrosum 6× HPUS; *Sanguinaria Canadanensis* 12× HPUS; *Lachesis Muta* 12× HPUS; and at least 200 mg calcium provided as calcium citrate.

9. A method for treating menopausal symptoms in a patient exhibiting such symptoms comprising orally administering to the patient two tablets according to claim 2 twice daily for a total of 4 tablets daily.

* * * * *

UNITED STATES PATENT AND TRADEMARK OFFICE
CERTIFICATE OF CORRECTION

PATENT NO. : 6,248,307 B1
DATED : June 19, 2001
INVENTOR(S) : Borneman et al.

It is certified that error appears in the above-identified patent and that said Letters Patent is hereby corrected as shown below:

<u>Title page,</u>
Item [56] References Cited, U.S. PATENT DOCUMENTS,
Change "books." to -- books/ --.

Signed and Sealed this

Fifth Day of March, 2002

Attest:

JAMES E. ROGAN
*Attesting Officer*     *Director of the United States Patent and Trademark Office*